United States Patent [19]

Stienstra

[11] Patent Number: 4,961,732

[45] Date of Patent: Oct. 9, 1990

[54] ATHLETE'S FOOT BANDAGE

[76] Inventor: Christopher J. Stienstra, Box 899 (Monroe St.), E. Douglas, Mass. 01516

[21] Appl. No.: 309,492

[22] Filed: Feb. 13, 1989

[51] Int. Cl.⁵ .............................. A61M 35/00
[52] U.S. Cl. ................... 604/293; 128/157; 604/304; 604/307; 604/308
[58] Field of Search ............ 128/155, 156, 157; 604/293, 304, 307, 308

[56] References Cited

U.S. PATENT DOCUMENTS

| | | | |
|---|---|---|---|
| 3,529,597 | 9/1970 | Fuzak | 128/157 |
| 3,563,237 | 2/1971 | Maxwell | 128/165 |
| 3,565,075 | 2/1971 | Jerry | 128/157 |
| 3,934,582 | 1/1976 | Gorrie | 128/356 |
| 3,943,922 | 3/1976 | Umeda | 604/293 |
| 4,632,103 | 12/1986 | Fabricant et al. | 128/157 |
| 4,689,044 | 8/1987 | Murata | 128/155 |

FOREIGN PATENT DOCUMENTS 0811791 4/1959 United Kingdom ............... 604/293

OTHER PUBLICATIONS

The Merck Index (9th Ed.), Merck & Co. Inc., Rahway N.J., 1976, p. 309(2370), p. 1224(9216).

Primary Examiner—C. Fred Rosenbaum
Assistant Examiner—Michael Rafa
Attorney, Agent, or Firm—Leon Gilden

[57] ABSTRACT

An athlete's foot bandage is set forth utilizing a generally "T" shaped configuration for securement between adjacent toes of an individual. The bandage utilizes a first and second horizontally aligned first and second leg with a medially positioned downwardly depending shank therefrom having secured thereto a medicant pad secured to outer surfaces of the opposed sides of the shank spaced somewhat above lower terminal edges of the shank to position the treated pads to confronting surfaces of adjacent toes to simultaneously space the toes to prevent reinfection therebetween and apply an anti-fungal medicant to preselected areas.

2 Claims, 1 Drawing Sheet

U.S. Patent  Oct. 9, 1990  4,961,732
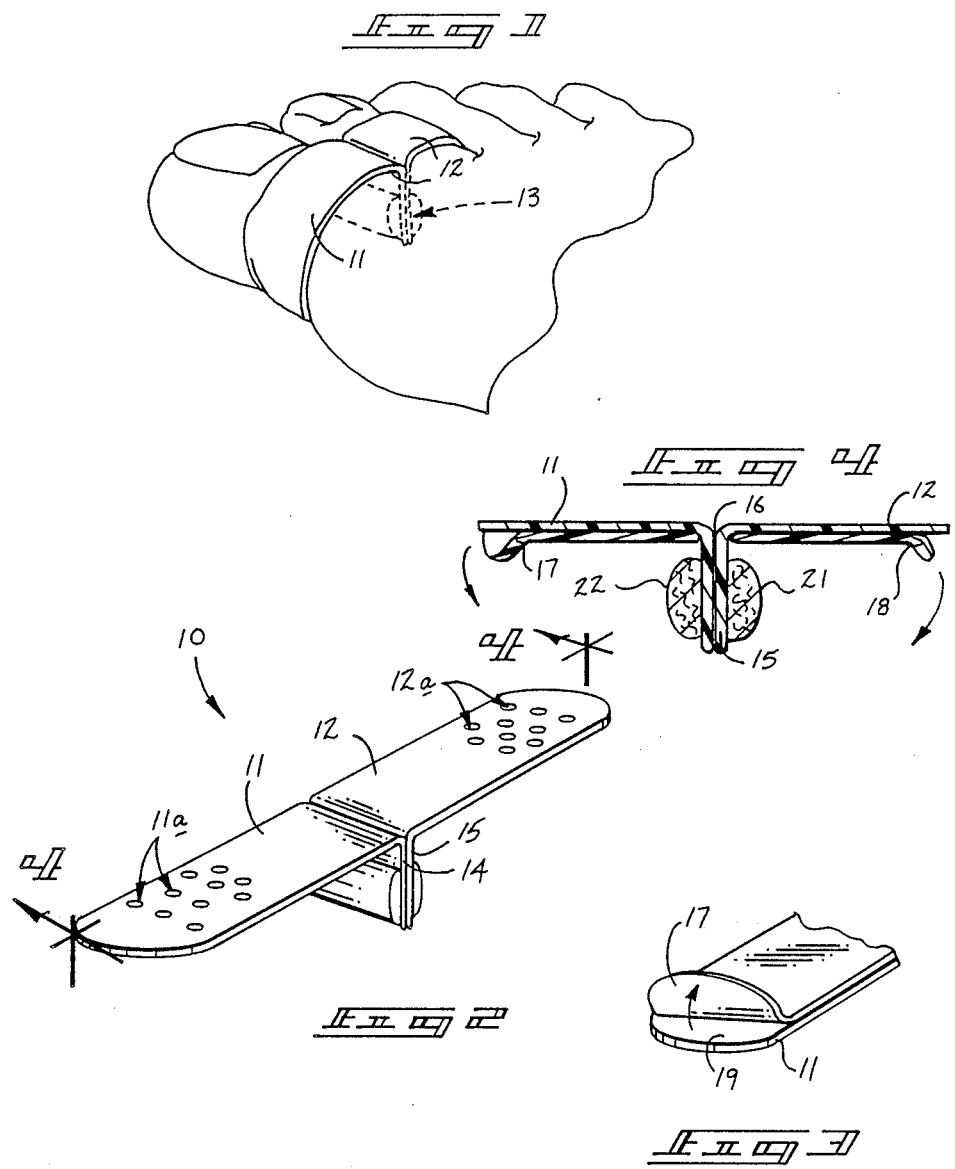

ATHLETE'S FOOT BANDAGE

BACKGROUND OF THE INVENTION

1. Field of the Invention

The field of invention relates to bandages, and more particular relates to a new and improved athlete's foot bandage wherein the same particularly positions a downwardly depending shank including a plurality of pads secured thereto to treat areas of adjacent toes of an individual to treat Tenia Pedis (athlete's foot).

2. Description of the Prior Art

The use of bandages of various configurations to treat infected areas of an individual is known in the prior ar&. The bandages of the prior art have heretofore failed to resolve the problem of properly spacing adjacent toes to avoid re-infection between the toes of a fungal infection such as Tenia Pedis, and further adequately applying medication to the infected areas. For example, U.S. Pat. No. 3,529,597 to Fuzak sets forth a fingertip bandage utilizing a plurality of optionally disposed wing-like segments provided with a releasable adhesive on facing sheets disposed on opposite sides of the aforenoted wing segments to treat and enclose a fingertip of an individual.

U.S. Pat. No. 3,568,287 to Maxwell sets forth a bandage for application to distal phalanxes utilizing a strip of adhesive coated material having arcuate longitudinal sides substantially parallel to one another.

U.S. Pat. No. 3,565,075 to Jerry sets forth a bandage construction utilizing a plurality of adhesive strips with a gauze pad adhered thereto with medication container connected between the strips to enable application of medication to the gauze pad portion of the bandage.

U.S. Pat. No. 3,984,582 to Gorrie sets forth a surgical wrap for preventing bacterial migration wherein the wrap is conformal to the contour of a foot it is secured to.

U.S. Pat. No. 4,632,108 to Fabricant sets forth a bandage construction for securement about a toe portion of a foot to apply treatment to bunion pain of the foot. The bandage is of a relatively complex organization related to that of the instant invention, but is of interest relative to the utilization of unique constructural configuration to apply bandage application to preselected portions of a foot.

As such, it may be appreciated that there is a continuing need for a new and improved athlete's foot bandage wherein the same sets forth a convenient organization to apply medicant to a user s foot while simultaneously maintaining separation between adjacent toes onto which the bandage is position to effect appropriate treatment of the foot.

SUMMARY OF THE INVENTION

In view of the foregoing disadvantages inherent in the known types of bandage organizations now present in the prior art, the present invention provides an athlete's foot bandage wherein the same may be conveniently stored when not in use and may be further easily and effectively secured to provide medication to adjacent toes of an individual. As such, the general purpose of the present invention, which will be described subsequently in greater detail, is to provide a new and improved athlete's foot bandage which has all the advantages of the prior art bandage devices and none of the disadvantages.

To attain this, the present invention comprises generally "T" shaped bandage utilizing a plurality of first and second legs horizontally aligned of mirror-like configuration relative to one another with a downwardly depending shank. The downwardly depending shank comprises first and second legs adhesively secured to one another with first and second pads secured onto exterior surfaces of the legs wherein the pads are positioned above lowermost edges of the legs. The pads are provided with an anti-fungal medicant to apply treatment to infected toe surfaces.

My invention resides not in any one of these features per se, but rather in the particular combination of all of them herein disclosed and claimed and it is distinguished from the prior art in this particular combination of all of its structures for the functions specified.

There has thus been outlined, rather broadly, the more important features of the invention in order that the detailed description thereof that follows may be better understood, and in order that the present contribution to the art may be better appreciated. There are, of course, additional features of &he invention that will be described hereinafter and which will form the subject matter of the claims appended hereto. Those skilled in the art will appreciate that the conception, upon which this disclosure is based, may readily be utilized as a basis for &he designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved athlete's foot bandage which has all the advantages of the prior art athlete's foot bandages and none of the disadvantages.

It is another object of the present invention to provide a new and improved athlete's foot bandage which may be easily and efficiently manufactured and marketed.

It is a further object of the present invention to provide a new and improved athlete's foot bandage which is of a durable and reliable construction.

An even further object of the present invention is to provide a new and improved athlete's foot bandage which is susceptible of a low cost of manufacture with regard to both materials and labor, and which accordingly is then susceptible of low prices of sale to the consuming public, thereby making such athlete's foot bandage economically available to the buying public.

Still yet another object of the present invention is to provide a new and improved athlete's foot bandage which provides in the apparatuses and methods of the prior art some of the advantages thereof, while simultaneously overcoming some of the disadvantages normally associated therewith Still another object of the present invention is to provide a new and improved athlete's foot bandage wherein the same simultaneously spreads and applies medicant to adjacent toes infected with Tenia Pedis.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is an isometric illustration of the instant invention secured to an individual's foot.

FIG. 2 is an isometric illustration of the instant invention.

FIG. 3 is an isometric illustration of one of the horizontal legs of the instant invention and the adhesive strip removably secured thereto.

FIG. 4 is an orthographic view taken in elevation of the instant invention

DESCRIPTION OF THE PREFERRED EMBODIMENT

With reference now to the drawings, and in particular to FIGS. 1 to 4 thereof, a new and improved athlete's foot bandage embodying the principles and concepts of the present invention and generally designated by the reference numeral 10 will be described.

More specifically, it will be noted that the athlete's foot bandage 10 essentially comprises a plurality of horizontally disposed and aligned legs including a first upper leg 11 and a second upper leg 12 wherein the legs are of generally elongate configuration positioned in an end to end orientation relative to one another with a downwardly depending first leg 14 and a respective downwardly depending second leg 15 joined together by an adhesive 16 to laminate the first and second downwardly depending legs together to define a shank 13 of the "T" shaped configuration of the athlete's foot bandage 10.

A respective first and second peel-away removable strip 17 and 18 is secured to underlying surfaces of the respective first and second upper legs 11 and 12 extending from outer terminal edges of the first and second upper legs 11 and 12 to the respective juncture of the first and second upper legs 11 and 12 to that of the downwardly depending first and second legs 14 and 15. The peel-away removable strips 17 and 18 expose a further adhesive 19 for securement of the bandage 10 to adjacent toes of a user, as illustrated in FIG. 1.

A first medicated pad 22 is secured to an exterior surface of the first downwardly depending leg 14 with a second medicated pad 21 positioned to an exterior surface of the second downwardly depending leg 15. The first and second medicated pads 22 and 21 are positioned above the lowermost terminal edges of the first and second downwardly depending legs 14 and 15 and below that of the juncture of the downwardly legs to that of the upper legs to enable application of a desired anti-fungal medicant to the adjacent surfaces of adjacent toes, as illustrated in FIG. 1. Anti-fungal medicant to treat Tenia Pedis may include Tolnftate (TM) or Clotrimazol as examples of desired anti-fungal treatment for the malady of athlete's foot.

The positioning of the pads below the respective junctures of the first and second upper legs 11 and 12 to that of the first and second downwardly depending legs 14 and 15 and above the lower terminal edges of the downwardly depending legs 14 and 15 positions the medicant to enable simultaneously treating of a desired predetermined area and spacing or spreading of the infected toes while avoiding wastage of medicant to areas that may not be accessible by the instant invention.

Further, it is understood that the pad is to be formed of fibrous or polymeric material as may be the upper and downwardly extending legs of the invention. Further, FIG. 1 illustrates a matrix of apertures 11a and 12a are through-extending in the respective first and upper legs 11 and 12 to enhance securement and grasping of the respective first and second upper legs during application of the aforenoted legs to an individual foot.

As to the manner of usage and operation of the instant invention, the same should be apparent from the above disclosure and accordingly no further discussion relative to the manner of usage and operation of the instant invention shall be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A bandage particularly for the application of an anti-fungal medication to confronting surfaces of adjacent toes of a foot comprising, a first elongate upper leg secured adjacent a second elongate upper leg, and a first downwardly extending lower leg contiguously secured to and coextensive with an adjacent second downwardly extending leg, and said first elongate upper leg joined to said first downwardly extending lower leg at a first junction, and said second elongate upper leg joined to said second downwardly extending lower leg at a second junction, and a first medicated pad secured to an exterior surface of said first leg, and a second medicated pad secured to an exterior surface of said second leg wherein said medicated pads are oriented for application of said anti-fungal medication to said surfaces, and wherein said first elongate upper leg is secured in a mirror image orientation adjacent said second elongate upper leg with said first and second junctions secured adjacent one another, and wherein said first downwardly extending lower leg is secured to said second downwardly extending lower leg at interior surfaces of said first and second downwardly extending lower legs with an adhesive to secure said first and said second downwardly extending lower legs together, and wherein a first removable strip is secured to an interior surface of said first elongate upper leg extending between a distal end of said first elongate upper leg to said first junction, and a second peel-away removable strip secured to an interior surface of said second elongate upper leg and extending between a forward end of said second elongate upper leg and said second junction, and wherein said first pad is secured to said exterior surface of said first leg above and spaced from a lowermost edge of said first downwardly extending lower leg and spaced below said first junction, and said second medicated pad secured to said exterior surface of said downwardly extending lower leg spaced a distance from a lower edge of said second downwardly extending lower leg and spaced below said second junction, and wherein said bandage is of a "T" shaped configuration.

2. A bandage as set forth in claim 1 wherein said anti-fungal medication comprises clotrimazol.

* * * * *